United States Patent [19]

Yamada

[11] Patent Number: 5,316,009
[45] Date of Patent: May 31, 1994

[54] APPARATUS FOR MONITORING RESPIRATORY MUSCLE ACTIVITY

[75] Inventor: Yoshitsugu Yamada, Tokyo, Japan

[73] Assignee: Nihon Kohden Corporation, Tokyo, Japan

[21] Appl. No.: 907,399

[22] Filed: Jul. 1, 1992

[30] Foreign Application Priority Data

Jul. 5, 1991 [JP] Japan ................................ 3-191205

[51] Int. Cl.⁵ .......................................... A61B 5/087
[52] U.S. Cl. .................................... 128/716; 128/720; 128/725; 128/204.23; 128/205.23
[58] Field of Search ........... 128/716, 720, 725, 204.23, 128/205.23

[56] References Cited

U.S. PATENT DOCUMENTS

| | | | |
|---|---|---|---|
| 4,031,885 | 6/1977 | Davis et al. | 128/720 |
| 4,444,201 | 4/1984 | Itoh | 128/725 |

OTHER PUBLICATIONS

Excerpt from the 38th General Meeting of Japan Society of Anesthesiology held on Mar. 28–30, 1991.
Excerpt from the 39th General Meeting of Japan Society of Anesthesiology held on Apr. 9–11, 1992.

*Primary Examiner*—Lee S. Cohen
*Attorney, Agent, or Firm*—Hoffmann & Baron

[57] ABSTRACT

A respiratory muscle activity monitoring apparatus is provided with a pressure sensor for detecting pressure in an air passage connecting a lung ventilator and the airway system of a patient and a flow rate sensor for detecting flow rate in the air passage. An arithmetic constant detecting unit detects resistance Rrs and elastance Ers of the respiratory system including the airway and thorax beforehand by using detection signals from the pressure sensor and the flow rate sensor while the lung ventilator is supplying air to the patient whose spontaneous breathing is temporarily stopped. Using airway opening pressure Paw detected by the pressure sensor and flow rate $dV/dt$ detected by the flow rate sensor, a developed pressure calculating unit calculates pressure Pmus developed by the respiratory muscles during mechanical ventilation as well as during spontaneous breathing from the expression: $Pmus = -Paw + Rrs(dV/dt) + Ers \int (dV/dt)dt$. An output unit displays and/or records the obtained Pmus together with waveform signal detected by the pressure sensor along a common time axis. Furthermore, by detecting a tidal volume VT from flow rate, work Wmus is calculated as follows: $Wmus = -\int Paw(dV/dt)dt + \int Rrs(dV/dt)^2 dt + (\frac{1}{2})Ers(VT)^2$

9 Claims, 3 Drawing Sheets

INSPIRATORY PHASE

APPARATUS FOR MONITORING RESPIRATORY MUSCLE ACTIVITY

BACKGROUND OF THE INVENTION

1. Field of the Invention

The present invention relates to a monitor apparatus for monitoring activity of the respiratory muscles of a patient whose breathing is partially supported by a lung ventilator which interacts with patient's respiratory muscles.

2. Description of the related Art

In a case where a lung ventilator is used, particularly in pressure support ventilation (PSV) mode, on a patient who manages to breathe spontaneously, the PS level and the amount of air supplied by the lung ventilator must be adjusted suitably to the condition of the patient so as to promote the spontaneous breathing and, at the same time, substantially prevent fatigue of the patient's respiratory muscles.

Figures 6, 7:
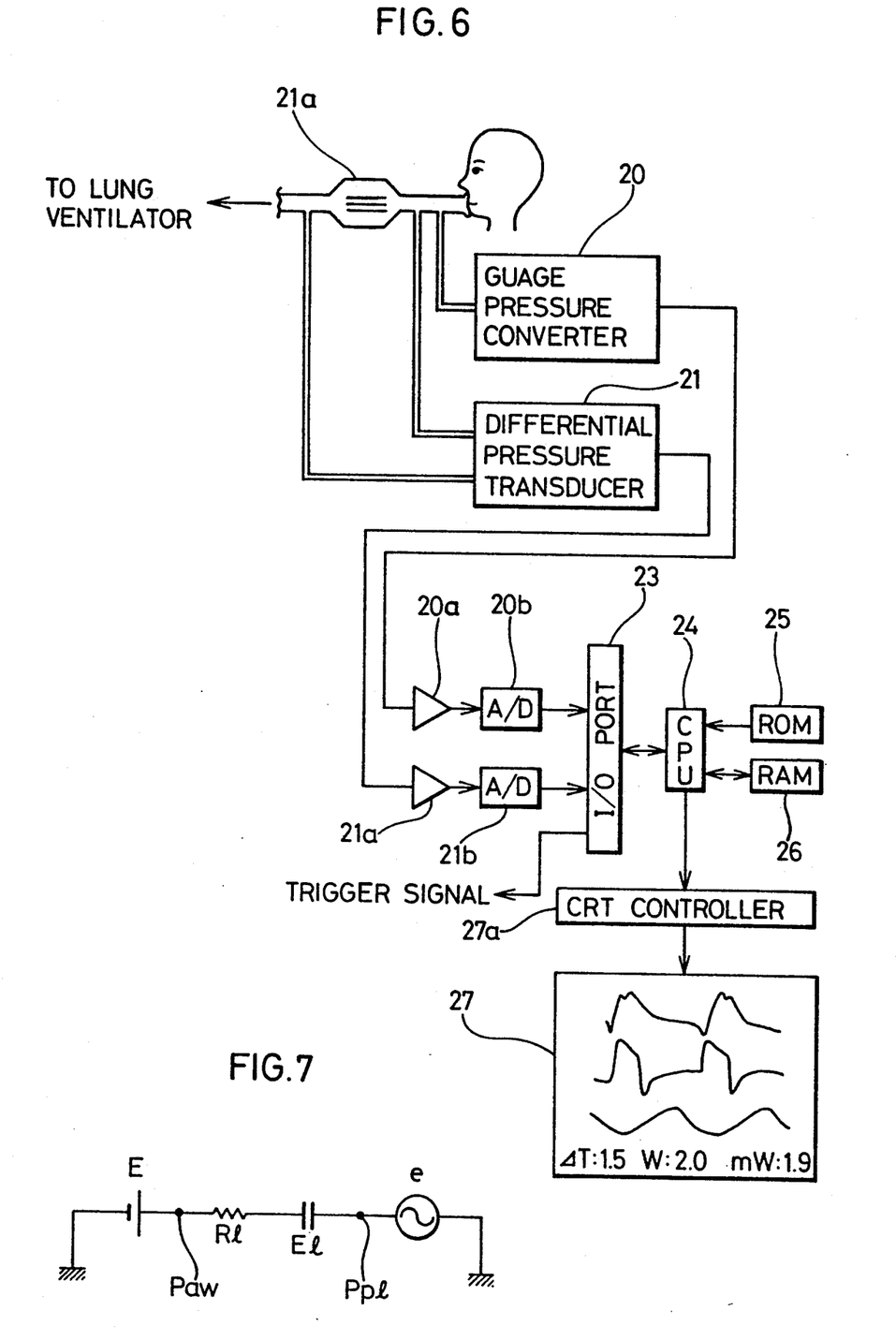
FIG. 6 illustrates the construction of a respiratory monitor apparatus, according to another embodiment of the present invention.
FIG. 7 illustrates a conventional equivalent circuit of the respiratory system.

In usual practice, the operational conditions of a lung ventilator are determined according to the physical conditions of the patient, such as blood gases, the respiration rate and the volume of ventilation, which are being monitored. A paper "Mathematical Model of Pressure Support Ventilation—an Explication of Mechanical Interaction between a Lung Ventilator and Respiratory Muscles," presented by the present inventors in the 38th Annual Meeting of Japan Society of Anesthesiology, Mar. 28, 1991, suggests that the work of respiratory muscles can be obtained by assuming an equivalent circuit of the respiratory system connected with a lung ventilator, as shown in FIG. 7. In the figure, E is a pressure of the supplied air, e is a spontaneous breathing source of a lung, Paw is an air pressure at the airway opening, Rl is an air flow resistance of the lung, and El is an elastance (an inverse of the compliance C) of the lung. A pressure inside a thoracic cavity Ppl is measured with assistance of a balloon catheter inserted in the patient's esophagus. An air-flow rate dV/dt is detected by a flow rate sensor which is installed in an air passage of the lung ventilator connected to the respiratory system. Patient's work W is calculated by integrating the value calculated by multiplication of the pressure and flow rate, as below $$W = \int -Ppl dV/dt dt$$

However, such a method of obtaining the work has several problems. The method is invasive. Measurement precision is not satisfactory since the work performed by the respiratory muscles to drive the thorax is not considered in the method. Further, supplying air of the lung ventilation may sometimes be late for the initiation of inspiration performed by the respiratory muscles, in which case the work performed by the respiratory muscles is wasted. There has not been developed a method to monitor the timing of the inspiratory activity of the respiratory muscles in order to initiate air-supplying of the lung ventilator exactly when PS level is developed.

SUMMARY OF THE INVENTION

It is an object of the present invention to provide an apparatus for monitoring respiratory muscle activity and, particularly, for monitoring in a noninvasive manner the timing of respiratory muscle pressure and airway opening pressure during air-supplying by a lung ventilator through assuming a more precise equivalent circuit.

It is another object of the present invention to provide an apparatus for monitoring respiratory muscle activity and, particularly, for measuring, in a noninvasive manner and with high precision, work performed by the respiratory muscles of a patient on a lung ventilator, including work performed by the respiratory muscles for the thorax on the premise of a precise equivalent circuit for the respiratory system because it has been verified that ignoring such work for the thorax will cause a substantially large error.

Figure 2:
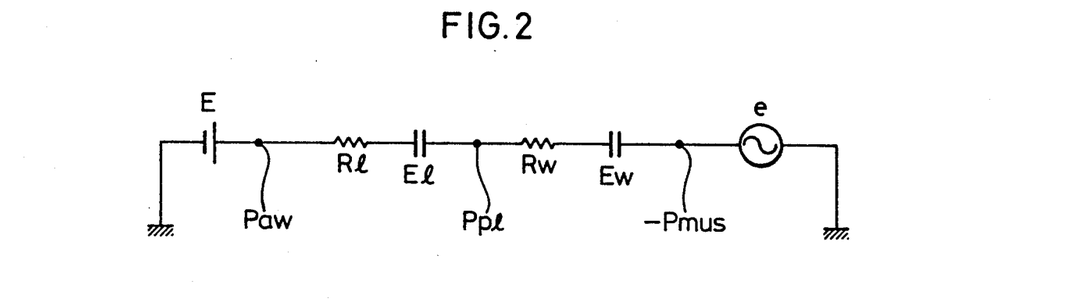
FIG. 2 illustrates an equivalent circuit of the respiratory system, on which the present invention is based.

According to the present invention, pressure developed by the respiratory muscles Pmus and work performed by the respiratory muscles Wmus are defined as below, based on equivalent circuit shown in FIG. 2 which includes air-flow resistance of the thorax Rw and elastance of the thorax Ew as well as the components of the conventional equivalent circuit shown in FIG. 7.

$$Wmus = \int Pmus(dV/dt)dt \qquad (1)$$

Using resistance of the respiratory system $Rrs = Rl + Rw$, elastance of the respiratory system $1/Crs = Ers = El + Ew$ and a lung volume change $\Delta S$, pressure at the elastance of the respiratory system is obtained as $\Delta S/Crs = Ers\Delta S$. Therefore, Pmus is $$\begin{aligned} Pmus &= -Paw + Rrs(dV/dt) + Ers\Delta S \\ &= -Paw + Rrs(dV/dt) + Ers\int(dv/dt)dt \end{aligned} \qquad (2)$$

Thereby, Pmus, which varies as the respiratory muscles contract, is continuously detected, and Wmus is obtained as $$Wmus = \int(-Paw + Rrs(dV/dt) + Ers\Delta S)dt \, dV/dt \qquad (3)$$

The same expression can be written $$Wmus = -\int Paw(dV/dt)dt + Rrs\int(dV/dt)^2 dt + Ers\int \Delta S dt \, dV/dt \qquad (4)$$

Since the amount of energy stored at the elastance is $$Ers\int \Delta S dt \, dV/dt = (\tfrac{1}{2})Ers(\Delta S)^2$$

the expression (4) can be written $$Wmus = -\int Paw(dV/dt)dt + Rrs\int(dV/dt)^2 dt + (\tfrac{1}{2})Ers(\Delta S)^2 \qquad (5)$$

Since $\Delta S$ over an inspiratory period is a tidal volume VT, $$Wmus = -\int Paw(dV/dt)dt + Rrs\int(dV/dt)^2 dt + (\tfrac{1}{2})Ers(Vt)^2 \qquad (6)$$

In the expressions (2) and (6), Paw, dV/dt, Rrs, Ers and VT are all parameters which can be measured or calculated utilizing a flow rate sensor and a pressure sensor that are mounted to an air passage connecting the external lung ventilator and the airway system of a patient. Therefore, to achieve the above-mentioned objects, the present invention provides a monitor apparatus comprising: a pressure sensor for detecting air pressure in an air passage connecting a lung ventilator and the airway system of a patient; a flow rate sensor for detecting flow rate in the air passage; an arithmetic constant detecting means for detecting resistance Rrs and elastance Ers of the respiratory system including the airway and thorax beforehand by using detection signals from the pressure sensor and the flow rate sensor while the lung ventilator is supplying air to the patient whose spontaneous breathing is temporarily stopped; a developed pressure calculating means for calculating pressure Pmus developed by the respiratory muscles during mechanical ventilation from the foregoing expression (2) using airway opening pressure Paw detected by the pressure sensor and flow rate dV/dt detected by the flow rate sensor; and a means for displaying and/or recording the obtained Pmus together with waveform signal detected by the pressure sensor along a common time axis.

Since data about a waveform of the respiratory muscle pressure can be obtained in such an apparatus, the timing of operation of a lung ventilator can be adjusted with respect to the actual inspiratory initiation of the respiratory muscles, by comparing the data about the above waveform with airway opening pressure. Thus, unnecessary fatigue of the respiratory muscles can be substantially prevented.

A monitor apparatus according to the present invention may be provided with: a time difference calculating means for detecting a time point when the thus calculated Pmus starts to decrease as an inspiration initial point, detecting a time when the level of detection signal from the pressure sensor starts to increase as an air-supplying initial point, and obtaining a time difference between the inspiration initial point and the air-supplying initial point; and a means for displaying and/or recording data of the time difference. Thereby, the time difference between initiation of air-supplying from a lung ventilator and initiation of inspiratory activity of the respiratory muscles is made recognizable in digits.

Further, a monitor apparatus according to the present invention may be provided with: a pressure-time product calculating means for detecting a time point when the obtained Pmus starts to decrease as an inspiration initial point, detecting a time point when the obtained Pmus starts to increase as an inspiration terminal point, and calculating pressure-time product between the inspiration initial point and the inspiration terminal point from the expression $PTP = \int Pmus \, dt$; and a means for displaying and/or recording data of the pressure-time product. Thereby, an index of the amount of oxygen consumed by the respiratory muscles, including the amount of oxygen consumed for isometric contraction that occurs during initiation of inspiration of the patient, can be obtained without requiring a measurement of the pressure in the esophagus.

Still further, a monitor apparatus according to the present invention may be provided with an expiration initiation detecting means for detecting a time point when the obtained Pmus starts to increase as an expiration initial point and outputting a signal indicating initiation of expiration. Thereby, a trigger signal for stopping air-supplying in PSV (pressure support ventilation) mode can be outputted with exact timing.

Further, a monitor apparatus according to the present invention may be provided with: a work calculating means for calculating work Wmus performed by the respiratory muscles over an inspiratory period from the foregoing expression (6); and a means for displaying and/or recording the obtained Wmus. Thereby, actual work performed by the respiratory muscles of the patient on a lung ventilator, including the work performed for the thorax, can be obtained. In a case where lung ventilation is performed in PSV mode for a patient who is spontaneously breathing, the respiratory muscle work of the patient can be maintained at a moderate level and fatigue of the respiratory muscles can be substantially prevented by setting the PS level and a tidal volume suitable to the patient. This monitor apparatus allows noninvasive and continuous monitoring of the respiratory muscle activity.

Further objects, features and advantages of the present invention will become apparent from the following description of the preferred embodiments with reference to the attached drawings.

DESCRIPTION OF THE PREFERRED EMBODIMENTS

Figure 1:
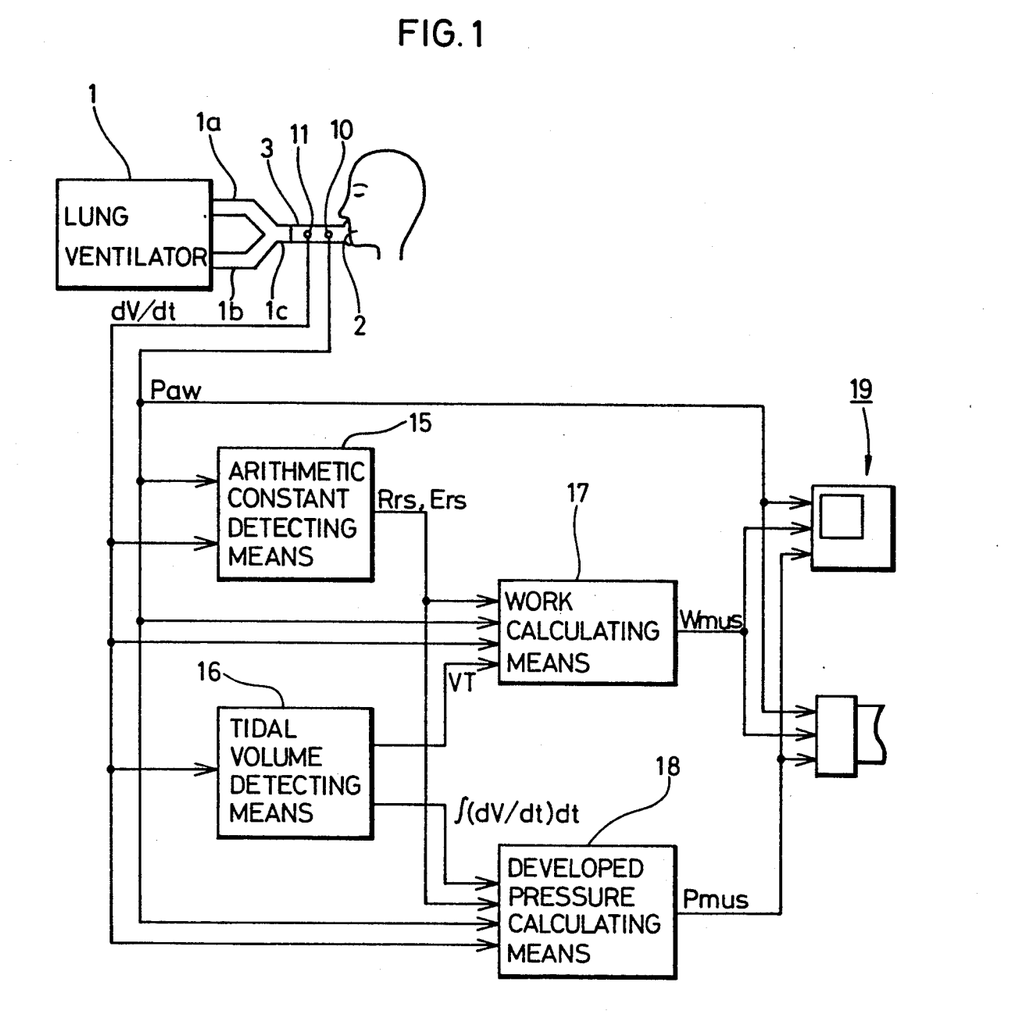
FIG. 1 illustrates the construction of a respiratory monitor apparatus, according to one embodiment of the present invention.

Referring to FIG. 1, showing the construction of an apparatus for monitoring respiratory muscle activity according to one embodiment of the present invention, a lung ventilator 1 triggers an air driving unit when pressure in an inspiratory air passage 1a reaches a predetermined negative pressure. The lung ventilator 1 also supports expiration through an expiratory air passage 1b. A common air passage 1c connecting to both of these air passages 1a and 1b is connected to an air passage 3, whose end is connected to an endotracheal tube 2. The air passage 3 is provided with a pressure sensor 10 for detecting pressure therein and a flow rate sensor 11 for detecting rate of the air flow therein.

The pressure sensor 10 and the flow rate sensor 11 are connected to: an arithmetic constant detecting means 15 for detecting Rrs and Crs or its inverse, i.e., Ers, by using detection signals from these sensors while the spontaneous breathing of a patient is temporarily stopped; a tidal volume detecting means 16 for obtaining a tidal volume VT by integrating dV/dt signal, which is detection signal from the flow rate sensor 11, over an inspiratory period between when the lung ventilator 1 starts supplying air, i.e., when the level of dV/dt signal starts rising, and when the lung ventilator 1 stops supplying air, i.e, when the level of dV/dt signal crosses zero, and by correcting the integrated value in accordance with the sectional area of the air passage; a work calculating means 17 for calculating work done by the respiratory muscles Wmus over an inspiratory period from the expression (6) using Paw signal, the dV/dt signal and VT signal; a developed pressure calculating means 18 for continuously calculating pressure developed by the respiratory muscles Pmus from the expression (2) using the Paw signal, the dV/dt signal and $\int(dV/dt)dt$ signal which is continuously supplied from the tidal volume detecting means 16. Output means 19 displays and/or records data of thus-obtained work in, e.g., a graphic or numerical values, and displays and/or records both a waveform of the amplified Paw signal and a waveform of data of Pmus using a common time axis.

Figure 3:
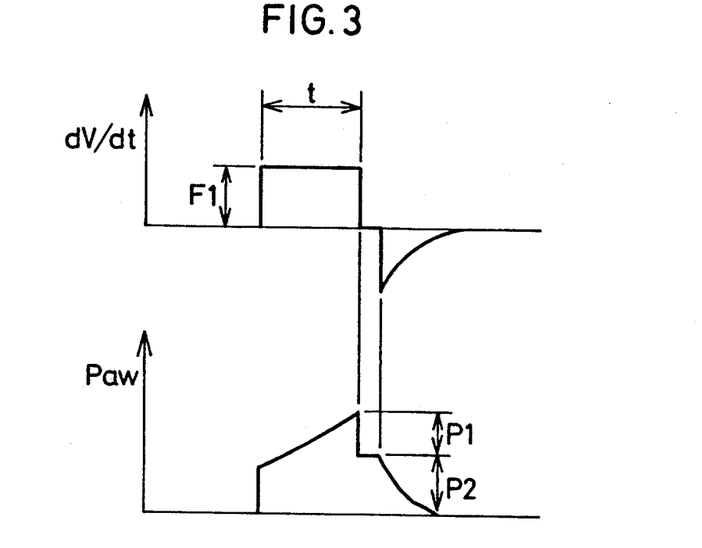
FIG. 3 shows waveforms for illustrating operations of the monitor apparatus of the above embodiment, the operation for measuring an arithmetic constant.

As shown in FIG. 3, the lung ventilator 1 supplies air at a constant level F1 of the flow rate dV/dt, and the pressure sensor 10 detects Paw while the patient's spontaneous breathing is temporarily stopped by, e.g., injecting a muscle relaxant into the patient. Then, the arithmetic constant detecting means 15 detects a pressure difference P1 between a peak pressure when air-supplying from the lung ventilator is finished and an end inspiratory pressure P2, and obtains Rrs= P1/F1. Further, the arithmetic constant detecting means 15 detects the end inspiratory pressure P2 and obtains Ers=P2/(F1×t), where t is a period of air-supplying, based on F1×t=P2×Crs.

The operation of the thus-constructed monitor apparatus will be described.

Figure 4:
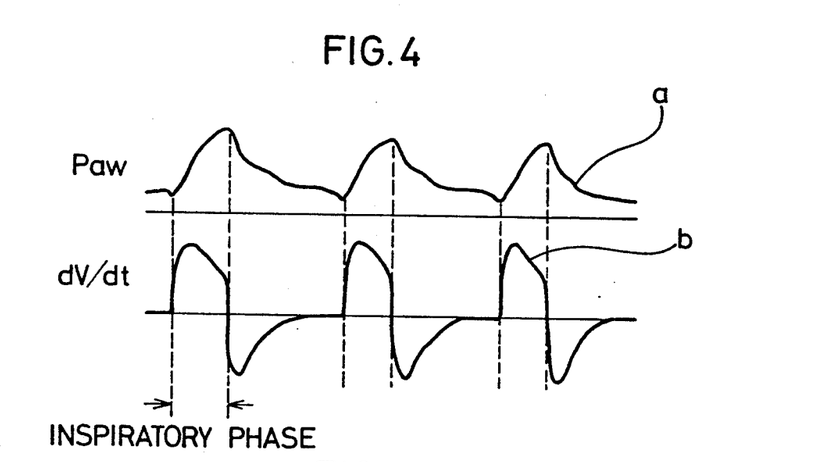
FIG. 4 shows waveforms for illustrating the operation of the monitor apparatus of the same embodiment.
Figure 5:
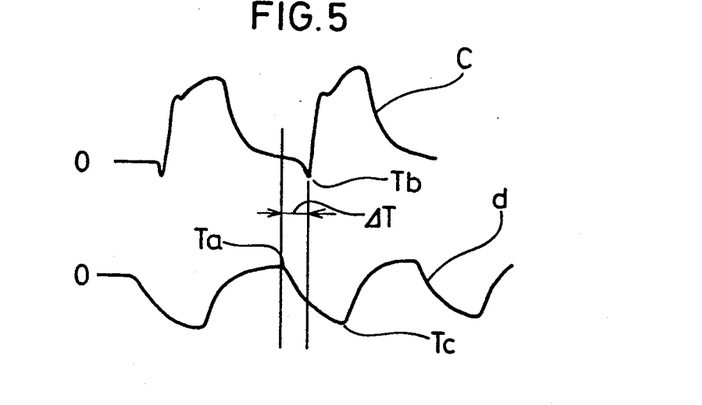
FIG. 5 shows monitoring waveforms of the monitor apparatus of the same embodiment.

When the endotracheal tube 2 connected to the lung ventilator 1 is connected to a patient, Rrs and Ers are measured as described above. The lung ventilator 1 is operated in PSV mode. The lung ventilator 1 is triggered to supply air when the airway pressure reaches a predetermined negative level. Supplying of air of a predetermined amount and at a predetermined flow rate is repeated, with an expiratory phase intervening. When the tidal volume calculating means 16 detects a sudden rise of waveform signal (b in FIG. 4) of detection signal dV/dt from the flow rate sensor 11 as initiation of inspiration, the tidal volume detecting means 16 starts integration for a tidal volume VT and serially supplies $\int(dV/dt)dt$ signals to the developed pressure calculating means 18. The termination of one period of air-supplying by the lung ventilator 1 is detected as a time point where dV/dt turns from positive to negative (corresponding to a sudden drop of the waveform signal of detection signal (a in FIG. 4) from the pressure sensor 10). At this point, the tidal volume calculating means 16 completes the operation for a tidal volume. Meanwhile, the work calculating means 17 calculates work Wmus over the inspiratory period from the expression (6) using the data serially inputted thereto. The developed pressure calculating means 18 calculates Pmus which continuously varies from the expression (2) using the data serially inputted thereto. The output means 19 displays the calculation waveform of Pmus (d in FIG. 5) together with the detection waveform of Paw (c in FIG. 5) practically without any delay and also the resultant Wmus of the calculation.

Through the above noninvasive manner, it can be determined whether the timing of initiation of air-supplying by the lung ventilator is appropriate with respect to the timing of initiation of inspiration. Work done by the respiratory muscles including work done to the thorax can be accurately measured without requiring insertion of a balloon catheter into the esophagus. Tests have shown that a known measuring method which ignores an equivalent parameter for a thorax provides a Measurement of respiratory muscle work at least 20% less than the actual value of the work.

FIG. 6 illustrates a monitor apparatus employing a CPU according to another embodiment of the present invention. A gauge pressure converter 20 detects Paw. A differential pressure transducer 21 detects dV/dt.

The Paw and dV/dt are amplified by amplifiers 20a, 21a and then digitized by A/D converters 20b, 21b, respectively. Then, the Paw and dV/dt are fed through an I/O port 23 to a CPU 24 as sample values. A ROM 25 stores programs for, e.g., calculation of the constants Rrs and Ers, calculation of a tidal volume VT, operation of the expression (2) using these data and data about airway opening pressure Paw and flow rate dV/dt, calculation of a time difference based on the result of that calculation, and operation of the expression (6), and further a program for output format. In accordance with these programs, the CPU 24 parallelly performs necessary operations using a RAM 26 which functions as a combination of the arithmetic constant detecting means, the developed pressure calculation means, the tidal volume detecting means and the work calculation means according to the present invention.

The CPU 24 also functions as a time difference calculating means. The CPU analyzes data of Paw and Pmus in order to detect a time point when Pmus starts decreasing (corresponding to Ta of d in FIG. 5) as a time point of initiation of inspiration and detect a time point when the level of Paw signal starts increasing (corresponding to Tb of c in FIG. 5) as a time point of initiation of air-supplying and then obtain a time difference $\Delta T$ between the two time points. Further, during the same work calculation, the CPU 24 functions as an expiration initiation detecting means. The CPU 24 detects a time point when Pmus starts increasing from the minimum level (corresponding to Tc of d in FIG. 5) as a time of initiation of expiration and sends a trigger signal to the lung ventilation for stopping air-supplying. The CPU 24 is connected with a CRT 27 which displays output data processed by the CPU 24 in a predetermined output format by control of a CRT controller 27a.

Therefore, while the lung ventilator is operated in inspiratory assist mode, the CRT 27 displays the waveforms of Paw, dV/dt and Pmus, from top to bottom in the figure, in predetermined formats and further displays the time difference $\Delta T$ and the work Wmus over the latest inspiratory period and the average work of a plurality of consecutive inspiratory periods in digit, for example, 1.5 sec, $2.0(10^{-2}$kg·m) and $1.9(10^{-2}$kg·m). Further, a trigger signal is outputted when expiration initiates.

To measure pressure-time product PTP as an index of the respiratory work load which is in correlation with the amount of oxygen consumed by the respiratory muscles at initiation of inspiration during mechanical ventilation, both of the foregoing embodiments may be provided with pressure-time integrating means for detecting a time point when Pmus starts to decrease and a time point when Pmus starts to increase as inspiration initial point Ta and inspiration terminal point Tc (equivalent to an expiration initial point), respectively, and obtaining the pressure-time product PTP over the duration between the two time points by integration $PTP = \int Pmusdt$, and output means for displaying and-/or recording the data of time-pressure products.

$\int Pmusdt$ is operated by, for example, sampling a value of Pmus every 10 msec between the time points Ta and TC and obtaining pressure-time product and adding such products. Alternatively, pressure-time product with respect to respiratory rate per minute may be obtained.

When a patient connected with a lung ventilator starts inspiration, the patient must lower pressure inside the thoracic cavity below that in the airway in order to open an inspiratory demand valve of the lung ventilator. However, during this isometric contraction until the inspiratory demand valve opens, inspiration is not performed. In the conventional art, pressure inside the esophagus must be measured and the measurement must be corrected with a chest-wall elastic contraction force in order to obtain a pressure-time product. On the other hand, according to the present invention, pressure-time product including chest-wall elastic contraction can be obtained without requiring a measurement of the esophageal pressure, as an index of the amount of oxygen consumed by the respiratory muscles including a period of isometric contraction. Thus, the variation of pressure-time product with time can be monitored.

A monitor apparatus according to the present invention can not only be provided in a stand-alone form but also be mounted inside a lung ventilator. In addition, an inspiratory phase can be detected using the pressure sensor and the flow rate sensor provided inside the lung ventilator. The monitor apparatus of the invention can also be used to perform mechanical ventilation through a nasal trachea or an incision in the trachea. The operation of a lung ventilator can be automatically controlled in accordance with the state of the respiratory muscle activity of the patient, by feeding back work signal and time difference signal to the lung ventilator.

While the present invention has been described with respect to what are presently considered to be the preferred embodiments, it is to be understood that the invention is not limited to the disclosed embodiments. To the contrary, the invention is intended to cover various modifications and equivalent arrangements included within the spirit and scope of the appended claims.

What is claimed is:

1. An apparatus for monitoring respiratory muscle activity comprising:
   a pressure sensor for detecting air pressure in an air passage connecting a lung ventilator and an airway system of a patient and generating a detection signal in response thereto;
   a flow rate sensor for detecting flow rate in said air passage and generating a detection signal in response thereto;
   arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
   developed pressure calculating means for calculating pressure Pmus developed by the respiratory muscles during lung ventilation from the following expression $$Pmus = -Paw + Rrs(dV/dt) + \int (dV/dt)dt$$

where Paw is airway opening pressure detected by said pressure sensor and dV/dt is flow rate detected by said flow rate sensor; and
   output means for outputting the obtained Pmus together with the detection signal generated by said pressure sensor along a common time axis.

2. An apparatus for monitoring respiratory muscle activity comprising:
   a pressure sensor for detecting air pressure in an air passage connecting a lung ventilator and an airway system of a patient and generating a detection signal in response thereto;
   a flow rate sensor for detecting flow rate in said air passage and generating a detection signal in response thereto;
   arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
   developed pressure calculating means for calculating pressure Pmus developed by the respiratory muscles during lung ventilation from the following expression $$Pmus = -Paw + Rrs(dV/dt) + \int (dV/dt)dt$$

where Paw is airway opening pressure detected by said pressure sensor and dV/dt is flow rate detected by said flow rate sensor;
   time difference calculating means for detecting a time point when the obtained Pmus starts to decrease as an inspiration initial point, detecting a time when the level of the detection signal generated by said pressure sensor starts to increase as a air-supplying initial point, and obtaining a time difference between said inspiration initial point and said air-supplying initial point; and
   output means for outputting data of said time difference.

3. An apparatus for monitoring respiratory muscle activity comprising:
   a pressure sensor for detecting air pressure in an air passage connecting a lung ventilator and an airway system of a patient and generating a detection signal in response thereto;
   a flow rate sensor for detecting flow rate in said air passage and generating a detection signal in response thereto;
   arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
   developed pressure calculating means for calculating pressure Pmus developed by the respiratory muscles during lung ventilation from the following expression $$Pmus = -Paw - Rrs(dV/dt) - \int (dV/dt)dt$$

where Paw is airway opening pressure detected by said pressure sensor and dV/dt is flow rate detected by said flow rate sensor;
   pressure-time product calculating means for detecting a time point when the obtained Pmus starts to decrease as an inspiration initial point, detecting a time point when the obtained Pmus starts to increase as an inspiration terminal point, and calculating pressure-time product between said inspiration initial point and said inspiration terminal point from the following expression $$PTP = \int Pmus\, dt;$$

and output means for outputting data of said pressure-time product.

4. An apparatus for monitoring respiratory muscle activity comprising:
a pressure sensor for detecting air pressure in air passage connecting a lung ventilator and an airway system of a patient and generating a detection signal in response thereto;
a flow rate sensor for detecting flow rate in said air passage and generating a detection signal in response thereto;
arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
developed pressure calculating means for calculating pressure Pmus developed by the respiratory muscles during lung ventilation from the following expression $$Pmus = -Paw + Rrs(dV/dt) + Ers\int(dV/dt)dt$$

where Paw is airway opening pressure detected by said pressure sensor and dV/dt is flow rate detected by said flow rate sensor; and
expiration initiation detecting means for detecting a time point when the obtained Pmus starts to increase as an expiration initial point and outputting a signal indicating initiation of expiration.

5. An apparatus for monitoring respiratory muscle activity comprising:
a pressure sensor for detecting air pressure in air passage connecting a lung ventilator and an airway system of a patient and generating a detection signal in response thereto;
a flow rate sensor for detecting flow rate in said air passage and generating a detection signal in response thereto;
arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
tidal volume detecting means for detecting a tidal volume by integrating said detection signal generated by said flow rate sensor;
work calculating means for calculating work Wmus performed by the respiratory muscles over an inspiratory period from the following expression $$Wmus = -Paw(dV/dt)dt + Rrs\int(dV/dt)^2 dt + (-\tfrac{1}{2})Ers(VT)^2$$

where Paw is airway opening pressure detected by said pressure sensor, dV/dt is flow rate detected by said flow rate sensor, and VT is a tidal volume detected by said tidal volume detecting means; and
output means for outputting the obtained work Wmus.

6. An apparatus for monitoring respiratory muscle activity according to claim 5, wherein said work calculating means calculates a mean value of work Wmus obtained in a plurality of inspiratory phases, and said output mean outputs said mean value.

7. An apparatus for monitoring respiratory muscle activity comprising:
a pressure sensor for detecting air pressure in an air passage connecting a lung ventilator and an airway system of a patient and generating a detection signal in response thereto;
a flow rate sensor for detecting flow rate in said air passage and generating a detection signal in response thereto;
arithmetic constant detecting means for detecting resistance Rrs and elastance Ers of a respiratory system of the patient including the airway and thorax beforehand by using the detection signal generated by said pressure sensor and the detection signal generated by said flow rate sensor while said lung ventilator is supplying air to the patient whose spontaneous breathing is temporarily stopped;
developed pressure calculating means for calculating pressure Pmus developed by the respiratory muscles during lung ventilation from the following expression $$Pmus = -Paw + Rrs(dV/dt) + Ers\int(dV/dt)dt$$

where Paw is airway opening pressure detected by said pressure sensor and dV/dt is flow rate detected by said flow rate sensor; and
output means capable of selectively outputting the generated detection signals of said pressure sensor and flow rate sensor and data calculated by said calculating means.

8. An apparatus for monitoring respiratory muscle activity as defined by claim 7, further comprising:
time difference calculating means for detecting a time point when the obtained Pmus starts to decrease as an inspiration initial pint, detecting a time when the level of detection signal from said pressure sensor starts to increase as a air-supplying initial point, and obtaining a time difference between said inspiration initial point and said air-supplying initial point and wherein the output means outputs data of said time difference.

9. An apparatus for monitoring respiratory muscle activity as defined in claim 7, further comprising:
expiration initiation detecting means for detecting a time point when the obtained Pmus starts to increase as an expiration initial point and wherein the output means outputs a signal indicating initiation of expiration.

* * * * *

UNITED STATES PATENT AND TRADEMARK OFFICE
CERTIFICATE OF CORRECTION

PATENT NO. : 5,316,009
DATED : May 31, 1993
INVENTOR(S) : Yoshitsugu Yamada

It is certified that error appears in the above-indentified patent and that said Letters Patent is hereby corrected as shown below:

| | |
|---|---|
| In Column 5, Line 63, | "Measurement" should read -- measurement --. |
| In Column 9, Line 12, | Phrase "pressure in air passage" should read --pressure in an air passage--. |
| In Column 10, Line 1 & 2 | Equation "Wmus=-Paw(dv/dt)+Rrs ∫ (dv/dt)²dt+ (-½)Ers(VT)²" should read: -- Wmus=- ∫ Paw(dv/dt)dt+Rrs ∫ (dv/dt)²dt+(½)Ers(VT)² --. |
| In Column 10, Line 49 | "pint" should read -- point --. |

UNITED STATES PATENT AND TRADEMARK OFFICE
CERTIFICATE OF CORRECTION

PATENT NO. : 5,316,009
DATED : May 31, 1993
INVENTOR(S) : Yoshitsugu Yamada

It is certified that error appears in the above-indentified patent and that said Letters Patent is hereby corrected as shown below:

In Column 10, Line 58,      Phrase "as defined in claim" should read:
--as defined by claim--.

Signed and Sealed this

First Day of November, 1994

*Attest:*

BRUCE LEHMAN

*Attesting Officer*      *Commissioner of Patents and Trademarks*